United States Patent [19]

Matsuo et al.

[11] Patent Number: 4,883,822

[45] Date of Patent: Nov. 28, 1989

[54] AGENT FOR REGULATING THE MOTIONAL FUNCTION OF GASTROINTESTINAL TRACT

[75] Inventors: Kohtaro Matsuo, Minoo; Youichirou Ezaki, Neyagawa; Akihiro Tobe, Yokohama; Satoshi Yamazaki; Kozue Enda, both of Machida; Mariko Kitsukawa, Fujisawa, all of Japan

[73] Assignees: Arakawa Chemical Industries, Ltd., Osaka; Mistubishi Kasei Corporation, Tokyo, both of Japan

[21] Appl. No.: 248,087

[22] Filed: Sep. 23, 1988

[30] Foreign Application Priority Data

Sep. 25, 1987 [JP] Japan ................................. 62-240247

[51] Int. Cl.$^4$ ............................................. A61K 31/12
[52] U.S. Cl. ..................................................... 514/680
[58] Field of Search ......................................... 514/680

Primary Examiner—Douglas W. Robinson
Assistant Examiner—Zohreh A. Fay
Attorney, Agent, or Firm—Oblon, Spivak, McClelland, Maier & Neustadt

[57] ABSTRACT

An agent for regulating the motional function of the gastrointestinal tract, which contains as an active ingredient a 4a-methyl-4,4a,9,10-tetrahydro-2(3H)-phenanthrenone derivative represented by the following formula I;

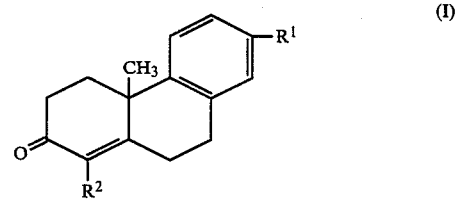

wherein $R^1$ represents a hydrogen atom, an alkyl group or an alkoxy group and $R^2$ represents a hydrogen atom or an alkyl group.

6 Claims, No Drawings

AGENT FOR REGULATING THE MOTIONAL FUNCTION OF GASTROINTESTINAL TRACT

BACKGROUND OF THE INVENTION

The present invention relates to an agent for regulating the motional function of the gastrointestinal tract.

Metoclopramide, Domperidone and so on have been previously known as agents for regulating the motional function of the gastrointestinal tract, which ameliorate symptoms of the alimentary canal such as nausea, emesis, anorexia, abdominal flatulence, epigastric dysphoria, abdominal pain and pyrosis caused by chronic gastritis, gastroptosis and postgastrectomy syndrome and during administration of levodopa or anticancer drug (European Journal of Pharmacology, 91, 197–205 (1983) and Japan Journal of Pharmacology, 39, 123–130 (1985)).

As a result of our energetic investigations for providing a compound having an activity for regulating the motional function of the gastrointestinal tract, it was found that 4a-methyl-4,4a,9,10-tetrahydro-2(3H)-phenanthrenone derivatives which are known as intermediates in the synthesis of dehydroabietic acid derivatives have an excellent level of the above-described activity.

SUMMARY OF THE INVENTION

The present invention provides an agent for regulating the motional function of the gastrointestinal tract, which contains as an active ingredient a 4a-metyl-4,4a,9,10-tetrahydro-2(3H)-phenanthrenone derivative represented by the following formula I;

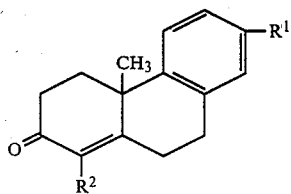
(I)

represents a hydrogen atom, an alkyl group or an alkoxy group and $R^2$ represents a hydrogen atom or an alkyl group.

The 4a-metyl-4,4a,9,10-tetrahydro-2(3H)-phenanthrenone derivative of the present invention is represented by the above-described formula I.

In the formula I, $R^1$ represents a hydrogen atom; an alkyl group such as a methyl, ethyl and propyl group; or an alkoxy group such as a methoxy and ethoxy group; and $R^2$ represents a hydrogen atom; or an alkyl group such as methyl and ethyl group. Among those groups, $R^1$ is preferably an alkyl group, particularly an isopropyl group, and $R^2$ is preferably a methyl group. The methyl group at the 4a-position of the phenanthrene ring may form either an optically active material or racemic material.

The 4a-methyl-4,4a,9,10-tetrahydro-2(3H)-phenanthrenone derivative of the present invention is a known compound and is described in, for example, Aust. J. Chem., 23(1), 93–105 (1970), Justus Liebigs Ann. Chem., 725, 154–166 (1969) and J. Am. Chem. Soc., 84, 284–292 (1962).

When the 4a-methyl-4,4a,9,10-tetrahydro-2(3H)-phenanthrenone derivative of the present invention is used as an agent for regulating the motional function of the gastrointestinal tract, the derivative can be administered orally or parenterally, however, oral administration is particularly preferred. Examples of drug forms that may be used for oral administration include solid forms such as a tablet, capsule and granules, and liquid forms such as a solution and suspension. Pharmaceutical preparation suitable for oral administration may contain pharmaceutically acceptable carriers or auxiliaries. Examples of carrier and auxiliary that may be used in solid forms such as a tablet and capsule include binder such as acacia, gelatin, dextrin, hydroxypropyl cellulose, methyl cellulose and polyvinylpyrrolidone; diluent such as lactose, saccharose, mannitol, corn starch, potato starch, calcium phosphate, calcium citrate and crystalline cellulose; lubricant such as magnesium stearate, calcium stearate, stearic acid, talc and silicic acid anhydride; disintegrator such as corn starch, potato starch, carboxymethyl cellulose, calcium carboxymethyl cellulose and alginic acid; and humectant such as sodium lauryl sulfate. Examples of carrier and auxiliary that may be used in liquid forms such as a solution and suspension include aqueous media such as water, suspending agent such as acacia, gelatin, methyl cellulose, sodium salt of carboxymethyl cellulose, hydroxymethyl cellulose and aluminium stearate gel; surfactant such as lecithin, sorbitan monooleate and glycerin monostearate; non-aqueous media such as glycerin, propylene glycol and vegetable oil. The medicament in liquid form also may contain preservative such as methyl p-hydroxybenzoate and propyl p-hydroxybenzoate; and flavoring agent and/or coloring agent.

The amount of the derivatives to be administered may variable depending on age, body weight and conditions of subject and specific disease to be cured, but 1 to 200 mg/kg, particularly 2 to 100 mg/kg per day is generally prefelable.

The 4a-methyl-4,4a,9,10-tetrahydro-2(3H)-phenanthrenone of the present invention has the activity for ameliorating symptoms of alimentary canal such as nausea, emesis, anorexia, abdominal flatulence, epigastric dysphoria, abdominal pain and pyrosis which are caused by chronic gastritis, gastroptosis and postgastrectomy syndrome and administration of levodopa or anticancer drug, and it is thus useful as an agent for regulating the motional function of the gastrointestinal tract.

EXAMPLES

The present invention will be described in detail hereinafter with reference to examples, but the examples do not limit the present invention and many variations and modifications can be made without departing from the scope of the invention.

EXAMPLE 1

Synthesis of (+)-1,4a-dimethyl-7-isopropyl-4,4a,9,10-tetrahydro2(3H)-phenanthrenone (Compound 1)

This compound was prepared from dehydroabietic acid in accordance with the method described in Aust. J. Chem., 23(1), 93–105 (1970).

$[\alpha]_D$: =193° (c, 1.05) (literature value: +196° (c, 0.23))

I.R. $\nu_{max}$ (CHCl$_3$): 1665 cm$^{-1}$ $^1$H NMR $\delta$(CDCl$_3$) 1.28 (6H, d, J=7 Hz), 1.52 (3H, s), 1.84 (3H, s), 6.94 (1H, s), 7.15 (2H, m)

$^{13}$C NMR δ(CDCl$_3$) 10.9 (q), 23.0 (q), 27.0 (q), 27.4 (t), 30.1 (t), 33.5 (d), 34.2 (t), 36.1 (t), 39.5 (s), 125.0 (d), 125.5 (d), 126.2 (d), 128.5 (s), 135.4 (s), 142.1 (s), 146.4 (s), 162.7 (s), 198.3 (s)

EXAMPLE 2

Synthesis of (±)-1,4a-dimethyl-7-isopropyl-4,4a,9,10-tetrahydro2(3H)-phenanthrenone (Compound 2)

This compound was prepared in accordance with the method described in J. Am. Chem. Soc., 84, 284–292 (1962).

Boiling point 147°–154° C. (0.05 Torr) (literature value: 165°–175° C. (0.04 Torr), 156°–164° C. (0.15 Torr)) I.R. $\nu_{max}$ (CHCl$_3$) 1665 cm$^{-1}$ $^1$H NMR δ(CDCl$_3$) 1.25 (6H, d, J=7 Hz), 1.52 (3H, s), 1.84 (3H, s), 6.94 (1H, s), 7.15 (2H, m)

$^{13}$C NMRδ(CDCl$_3$) 10.9 (q), 23.0 (q), 27.0 (q), 27.4 (t), 30.1 (t), 33.5 (d), 34.2 (t), 36.1 (t), 39.5 (s), 125.0 (d), 125.5 (d), 126.2 (d), 128.5 (s), 135.4 (s), 142.1 (s), 146.4 (s), 162.7 (s), 198.3 (s)

EXAMPLE 3

Synthesis of (±)-1,4a-dimethyl-4,4a,9,10-tetrahydro-2(3H)-phenanthrenone (Compound 3)

Potassium hydroxide in the amount of 2.24 g (40 mmol) was dissolved in 50 ml of 90 % methanol in 100-ml three-necked flask, and the obtained solution was then cooled with ice under agitation in a stream of nitrogen gas. A methanol solution (8 ml) containing 5.17 g (32 mmol) of 1-methyl-2-tetralone was added dropwisely to the above obtained solution over a period of 10 minutes. The reaction vessel was then cooled to −15° C., and 2.67 g (31 mmol) of ethyl vinyl ketone was added dropwisely to the reaction vessel. The temperature of the resulted mixture was brought to room temperature over a period of 4 hours under agitation in a stream of nitrogen gas. The mixture had been allowed to stand over night, and then the mixture was refluxed under heating for 3 hours in an atmosphere of nitrogen gas. After the temperature of the mixture had been brought to room temperature, the mixture was made acidic with hydrochloric acid and then extracted with ether. The ether layer was removed and washed with water, and then dried with sodium sulfate. The ether was distilled off to obtain 7.27 g of oily yellow residue. This residue was allowed to stand to obtain 5.54 g of crystals. These crystals were recrystallized twice from cyclohexane to obtain 3.95 g of colorless needle-like crystals.

Melting point 84°–85° C.

I.R. $\nu_{max}$ (CHCl$_3$): 1665 cm $^1$H NMR δ(CDCl$_3$): 1.57 (3H, s), 1.88 (3H, s), 7.1–7.4 (4H, m)

$^{13}$C NMR δ(CDCl$_3$): 11.4 (q), 27.5 (q), 27.9 (t), 30.5 (t), 34.7 (t), 36.7 (t), 40.2 (s), 126.1 (d), 126.5 (d), 127.3 (d), 128.9 (d), 129.1 (d), 136.1 (s), 145.3 (s), 162.7 (s), 196.7 (s)

EXAMPLE 4

Synthesis of (±)-4a-methyl-4,4a,9,10-tetrahydro-2(3H)-phenanthrenone (Compound 4)

Potassium hydroxide in the amount of 2.25 g (40 mmol) was dissolved in 4.5 g of water in 100-ml three-necked flask, and the obtained solution was then cooled with ice under agitation in a stream of nitrogen gas. A methanol solution (8 ml) containing 4.8 g (30 mmol) of 1-methyl-2-tetralone was added dropwisely to the above obtained solution. The reaction vessel was cooled to −15° C., then, 2.1 g (30 mmol) of methyl vinyl ketone was added dropwisely to the reaction vessel and 2 ml of methanol was further added thereto. The resulted mixture was agitated under cooling with ice for 1 hour and then at room temperature for 6 hours in a stream of nitrogen-gas. Then, the mixture had been allowed to react at 70° C. for 6 hours. The reaction mixture was then poured into iced water, made acidic with hydrochloric acid and extracted with ether. The ether layer was removed and washed with water, and then dried with sodium sulfate. The ether was distilled off to obtain 5.75 g of oily yellowish orange residue. A part of this residue was crystallized and resulted crystals were recrystallized twice from cyclohexane to obtain 2.8 g of colorless plate-like crystals. The oily portion was further allowed to crystallize to obtain 1.9 g of crystals. The total yield was 4.7 g.

Melting point: 88°–90° C. (literature value: 89°–90° C., Journal of Organic Chemistry, 44, 2746 (1979))

I.R. $\nu_{max}$ (CHCl$_3$): 1680 cm$^{-1}$ $^1$H NMR δ(CDCl$_3$): 1.48 (3H, s), 5.91 (1H, s), 7.1–7.3 (4H, m)

$^{13}$C NMR δ(CDCl$_3$): 27.6 (q), 31.1 (t), 34.7 (t), 36.1 (t), 39.1 (s), 124.2 (d), 126.1 (d), 126.9 (d), 128.7 (d), 134.7 (s), 143.7 (s), 169.6 (s), 198.9 (s)

EXAMPLE 5

Ability to improve the Dopamine induced reduction of gastric emptying rate

The ability of the medicament according to the invention, to improve the reduction of gastric emptying rate induced by intraperitoneal administration of Dopamine at the dose of 30 mg/kg in male ddy mice (body weight: 25 to 30 g), was determined.

The mice, which had been previously fasted for 24 hours before the start of the experiments, were fed with solid feed during 3 hours. Then, the mice were administered orally with a suspension of the compound obtained Example 1 (Compound 1) in 1 % Tween solution (3 mg/ml) at the dose of 0.1 ml per 10 g of the body weight, and intraperitoneally with a solution of Dopamine in a physiological saline (3 mg/ml) at the dose of 0.1 ml per 10 g of the body weight, simultaneously. After the administration, the mice were left for 1 hour with no feed and no water and then killed by dislocation of cervical vertebrae. The total weight of the stomach of each mouse including the content thereof was measured. The gastric output was represented by the difference between the average weight of the stomach of the mice killed immediately after the feeding of 3 hours and that of the mice killed at 1 hour later from the administration of Dopamine and the compound according to the invention. The improvement ratio of the reduction of gastric emptying rate was calculated in accordance with the following equation:

$$\text{Improvement Ratio (\%)} = \frac{GO_1 - GO_2}{GO_3 - GO_2} \times 100$$

$GO_1$: Gastric output of the mice administered with the compound of the invention and Dopamine $GO_2$: Gastric output of the mice administered with Dopamine $GO_3$: Gastric output of the control mice

| Treatment | N | Gastric Output (mg) | Improvement Ratio (%) |
| --- | --- | --- | --- |
| No treatment | 10 | 1070 ± 79 | — |
| Intraperitoneal administration of 30 mg/kg of Dopamine | 10 | 458 ± 73 | — |
| Intraperitoneal administration of 30 mg/kg of Dopamine + Oral administration of 30 mg/kg of Compound 1 | 10 | 708 ± 92 | 40.8 |

EXAMPLE 6

Effect on intragastric pressure

The effect of the compound on the gastric motion was investigated by measuring the intragastric pressure of male Donryu rats (body weight: 250 to 300 g) using the balloon method. Each of the rats, which had been fasted for 24 hours previously, was etherized and subjected to laparotomy, and a rubber balloon (diameter: 1 cm) filled with distilled water was introduced into the stomach from the incision at the forestomach. The intragastric pressure was recorded on a polygraph by means of a pressure transducer connected to the balloon via a catheter. After each of the rats had completely awakened and reproducible contraction pressure of the normal level was obtained, the effect of the medicament was determined. The activity of the medicament was determined by measuring the ability to improve a significant reduction of intragastric contraction pressure caused by continuous intravenous injection of Dopamine (50 μg/kg/hr).

Result

Compound 1 exhibited a significant improving effect with the intravenous administration of 3 mg/kg of the compound.

EXAMPLE 7

Effect on isolated ileum of guinea pig

Male Hartley guinea pigs (body weight: 300 to 500 g) were killed by cephalic assault and dehematization. Then the ileum with a length of about 3 cm was removed from each of the animals and suspended in an organ bath containing the Krebs-Henseleit solution, and kept at a temperature of about 32° C. by circulation of a gas containing 95% $O_2$ and 5% of $CO_2$ Static tension of 1 g was loaded on the ileum and the isotonic contraction was recorded on a polygraph by means of an isotonic transducer.

After the segment had been stabilized, $10^{-5}$ M (bath concentration) of acetylcholine (Ach) was added to the segment to obtain the maximum contraction. After the specimen had been washed 3 to 4 times, Compound 1 was added to the bath cumulatively up to the concentration of $10^{-7}$ to $3 \times 10^{-4}$ M

Result

Compound 1 increased the contraction of the ileum dose-dependently from the concentration of $10^{-5}$ M, and the contraction at the concentration of $3 \times 10^{-4}$ M was 60.0±10.9 % based on the contraction at the concentration of $10^{-5}$ M of Ach taken as 100 %.

EXAMPLE 8

Effect on action of isolated ileum of guinea pig caused by electrical stimulation (Transmural Stimulation)

Male Hartley guinea pigs (body weight: 300 to 500 g) were killed by cephalic assault and dehematization. Then the ileum with a length of about 3 cm was removed from each of the animals and suspended in an organ bath containing the Krebs-Henseleit solution, and kept at a temperature of about 32° C. by circulation of a gas containing 95% $O_2$ and 5% of $CO_2$. Resting tension of 1 g was loaded on the ileum and the variation of isometric tension was recorded on a polygraph by means of an FD pickup. Two platinum wires were used as stimulating electrodes, one of them was placed at the inside of the ileum and the other was soaked in the nutrient solution at the outside of the ileum.

After the segment had been stabilized, electrical stimulation of 0.1 Hz and 0.5 ms under the conditions capable of causing the maximum contraction was applied on the segment to obtain a constant contraction. Then, Compound 1 was added to the bath cumulatively up to the concentration of $4 \times 10^{-8}$ to $4 \times 10^{-5}$ M.

The activity of Compound 1 was represented as the variation ratio of the contraction calculated on the basis of the contraction before the addition of Compound 1 taken as 100 %.

Result

Compound 1 increased the contraction caused by electrical stimulation from the concentration of $4 \times 10^{-7}$ M, and the contraction at the concentration of $4 \times 10^{-5}$ M was 123.0±4.7 %.

EXAMPLE 9

Effect on isolated rat fundus of strips

Wister male rats (body weight: 200 to 300 g) fasted for a night were used. They were killed by cephalic assault and dehematization, and the stomach was removed and incised along the greater curvature thereof to prepare a strip of about 5 mm × 20 mm of the fundus in accordance with the method described by Vane (Vane, J. R.: A sensitive method for the assay of 5-hydroxytryptamine, Brit. I. Pharmacol., 12, 344–349 (1957)). This strip was then suspended in an organ bath containing the Krebs-Henseleit solution passed through with a gas containing 95% $O_2$ and 5% of $CO_2$. Static tension of 1 g was loaded on the strip and the isotonic contraction was recorded on a polygraph by means of an isotonic transducer.

After the strips had been stabilized, $10^{-5}$ M of acetylcholine (Ach) was added to obtain the maximum contraction. After the segment had been washed 3 to 4 times, Compound 1 was added to the bath cumulatively up to the concentration of $10^{-7}$ to $10^{-4}$ M.

Result

Compound 1 increased the contraction of the strip dose-dependently from the concentration of $3 \times 10^{-7}$ M, and the contraction at the concentration of $10^{-4}$ M was 34.9±4.2 % based on the contraction at the concentration of $10^{-5}$ M of Ach taken as 100 %.

EXAMPLE 10

Acute Toxicity

A Tween suspension of Compound 1 was orally administered (P.O.) to each of ddy male mice (body weight: 20 to 25 g) in the ratio of 2 ml per 100 g of body weight. After the administration, the mice were freely fed with feed and water and the number of dead mice was counted.

| Dose (Compound 1) | Number of dead mice |
|---|---|
| 2000 mg/kg P.O. | 0/6 |
| 3000 mg/kg P.O. | 0/6 |

What is claimed is:

1. A composition for regulating the motional function of the gastrointestinal tract, comprising a therapeutically effective amount of a 4a-metyl-4,4a,9,10-tetrahydro-2(3H)-phenanthrenone derivative represented by the following formula I;

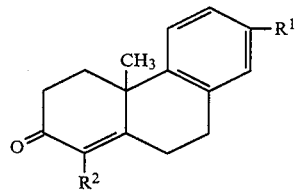

wherein $R^1$ represents a hydrogen atom, an alkyl group or an alkoxy group and $R^2$ represents a hydrogen atom or an alkyl group.

2. A composition according to claim 1, wherein $R^1$ represents an alkyl group.

3. A composition according to claim 2, wherein $R^1$ represents a isopropyl group and $R^2$ represents a methyl group.

4. A method for regulating the motional function of the gastrointestinal tract comprising administering a therapeutically effective amount of a 4a-methyl-4, 4a, 9, 10-tetrahydro-2 (3H)-phenanthyenone derivative represented by the formula I.

5. A method of claim 4, wherein $R^1$ represents an alkyl group.

6. A method of claim 5, wherein $R^1$ represents a isopropyl group and $R^2$ represents a methyl group.

* * * * *

UNITED STATES PATENT AND TRADEMARK OFFICE
CERTIFICATE OF CORRECTION

PATENT NO. : 4,883,822

DATED : Nov. 28, 1989

INVENTOR(S) : Kohtaro Matsuo, et al

It is certified that error appears in the above-identified patent and that said Letters Patent is hereby corrected as shown below:

Title page:

The second Assignee is incorrectly recorded, "Mistubishi Kasei Corporation" should be:

--Mitsubishi Kasei Corporation--

Signed and Sealed this

Eighth Day of January, 1991

Attest:

HARRY F. MANBECK, JR.

*Attesting Officer*     *Commissioner of Patents and Trademarks*